US011439975B2

(12) United States Patent
Laroche et al.

(10) Patent No.: US 11,439,975 B2
(45) Date of Patent: Sep. 13, 2022

(54) ZEOLITE ADSORBENTS BASED ON BARIUM, STRONTIUM, POTASSIUM AND SODIUM, PREPARATION PROCESS THEREFOR, AND USES THEREOF

(71) Applicants: Arkema France, Colombes (FR); IFP Energies Nouvelles, Rueil-Malmaison (FR)

(72) Inventors: Catherine Laroche, Vernaison (FR); Ludivine Bouvier, Orthez (FR); Javier Perez-Pellitero, Lyons (FR); Marie-Laurence Labede, Lescar (FR)

(73) Assignees: Arkema France, Colombes (FR); IFP Energies Nouvelles, Rueil-Malmaison (FR)

( * ) Notice: Subject to any disclaimer, the term of this patent is extended or adjusted under 35 U.S.C. 154(b) by 187 days.

(21) Appl. No.: 16/956,117

(22) PCT Filed: Dec. 17, 2018

(86) PCT No.: PCT/FR2018/053328
§ 371 (c)(1),
(2) Date: Jun. 19, 2020

(87) PCT Pub. No.: WO2019/122650
PCT Pub. Date: Jun. 27, 2019

(65) Prior Publication Data
US 2020/0316558 A1 Oct. 8, 2020

(30) Foreign Application Priority Data

Dec. 22, 2017 (FR) ..................... 1763033

(51) Int. Cl.
| | |
|---|---|
| *B01J 20/18* | (2006.01) |
| *B01D 15/18* | (2006.01) |
| *B01J 20/30* | (2006.01) |
| *C07C 7/13* | (2006.01) |
| *B01J 29/08* | (2006.01) |
| *B01J 35/02* | (2006.01) |
| *B01J 37/00* | (2006.01) |
| *C07C 15/04* | (2006.01) |
| *C07C 15/08* | (2006.01) |
| *C07C 15/02* | (2006.01) |
| *C07C 29/76* | (2006.01) |
| *C07C 15/06* | (2006.01) |
| *C07C 39/07* | (2006.01) |
| *C07C 211/50* | (2006.01) |
| *C07C 201/16* | (2006.01) |
| *C07C 205/06* | (2006.01) |

(52) U.S. Cl.
CPC ........ *B01J 20/186* (2013.01); *B01D 15/1821* (2013.01); *B01J 20/3028* (2013.01); *B01J 20/3078* (2013.01); *B01J 20/3085* (2013.01); *B01J 29/08* (2013.01); *B01J 29/082* (2013.01); *B01J 35/023* (2013.01); *B01J 37/0009* (2013.01); *C07C 7/13* (2013.01); *C07C 15/02* (2013.01); *C07C 15/04* (2013.01); *C07C 15/06* (2013.01); *C07C 15/08* (2013.01); *C07C 29/76* (2013.01); *C07C 39/07* (2013.01); *B01D 2253/108* (2013.01); *B01D 2253/1085* (2013.01); *B01J 2229/18* (2013.01); *B01J 2229/186* (2013.01); *B01J 2229/42* (2013.01); *C07C 201/16* (2013.01); *C07C 205/06* (2013.01); *C07C 211/50* (2013.01)

(58) Field of Classification Search
CPC ...... B01J 29/08; B01J 29/082; B01J 2229/42; B01J 2229/18; B01J 2229/186; B01J 20/18; B01J 20/186; B01J 20/28004; B01J 20/2803; B01J 20/3078; B01J 20/3028; B01J 20/3085; B01J 35/023; B01J 37/0009; C07C 7/13; C07C 15/06; C07C 15/08; C07C 15/04; C07C 15/02; C07C 29/76; C07C 37/82; C07C 39/07; C07C 205/06; C07C 201/16; C07C 211/50; B01D 15/1821; B01D 2253/108; B01D 2253/1085
USPC ............. 502/64, 69, 79, 400, 407, 411, 415; 585/804, 820, 825, 828, 831; 208/310 R, 208/310 Z
See application file for complete search history.

(56) References Cited

U.S. PATENT DOCUMENTS

| | | |
|---|---|---|
| 2,985,589 A | 5/1961 | Broughton et al. |
| 3,558,730 A | 1/1971 | Neuzil |
| 3,558,732 A | 1/1971 | Neuzil |
| 3,663,638 A | 5/1972 | Neuzil |
| 3,960,774 A | 6/1976 | Rosback |
| 3,997,620 A | 12/1976 | Neuzil |
| 4,226,977 A | 10/1980 | Neuzil et al. |
| 4,255,607 A | 3/1981 | Miyake et al. |
| 4,402,832 A | 9/1983 | Gerhold |
| 4,498,991 A | 2/1985 | Oroskar |
| 4,935,580 A | 6/1990 | Chao et al. |
| 4,957,514 A | 9/1990 | Golden et al. |
| 5,019,667 A | 5/1991 | Chao et al. |
| 5,177,299 A | 1/1993 | McCulloch et al. |
| 5,284,992 A | 2/1994 | Hotier et al. |
| 5,629,467 A | 5/1997 | Hotier et al. |
| 5,916,836 A | 6/1999 | Toufar et al. |

(Continued)

FOREIGN PATENT DOCUMENTS

| | | |
|---|---|---|
| CN | 1047489 A | 12/1990 |
| CN | 107206349 A | 9/2017 |

(Continued)

OTHER PUBLICATIONS

Non-Final Office Action for U.S. Appl. No. 16/955,400, dated Oct. 29, 2021, 14 pages.

(Continued)

*Primary Examiner* — Elizabeth D Wood
(74) *Attorney, Agent, or Firm* — RatnerPrestia

(57) ABSTRACT

The present invention relates to zeolite adsorbents based on agglomerated crystals of zeolite X comprising barium, potassium, sodium and strontium. These adsorbents have applications in the separation of fractions of aromatic C8 isomers and in particular xylenes.

21 Claims, No Drawings

(56) References Cited

U.S. PATENT DOCUMENTS

| | | |
|---|---|---|
| 6,143,057 A | 11/2000 | Bülow et al. |
| 6,884,918 B1 | 4/2005 | Plee et al. |
| 7,785,563 B2 | 8/2010 | Ryoo et al. |
| 9,919,289 B2 | 3/2018 | Bouvier et al. |
| 10,675,607 B2 | 6/2020 | Laroche et al. |
| 2011/0105301 A1 | 5/2011 | Wang |
| 2015/0306565 A1 | 10/2015 | Bouvier et al. |
| 2018/0201555 A1 | 7/2018 | LaRoche et al. |

FOREIGN PATENT DOCUMENTS

| | | |
|---|---|---|
| FR | 2329623 A1 | 5/1977 |
| FR | 2681066 A1 | 3/1993 |
| FR | 2789914 A1 | 8/2000 |
| GB | 909269 A | 10/1962 |
| JP | 4970877 A | 7/1974 |
| JP | 2002018242 A | 1/2002 |
| WO | 2013106816 A1 | 7/2013 |
| WO | 2014090771 A1 | 6/2014 |
| WO | 2016075281 A1 | 5/2016 |
| WO | 2017005907 A1 | 1/2017 |

OTHER PUBLICATIONS

Breck, D., "Zeolites Molecular Sieves", John Wiley & Sons, 1973, 4 pages.

Inayat et al., "Assemblies of Mesoporous FAU-Type Zeolite Nanosheets", Angew. Chem. Int. Ed., 2012, vol. 51, pp. 1962-1965.

International Search Report and Written Opinion for International Application PCT/FR2018/053327, dated Mar. 20, 2019, 9 pages.

International Search Report and Written Opinion for International Application PCT/FR2018/053328, dated Feb. 12, 2019, 9 pages.

Ruthven et al., "Principles of Adsorption and Adsorption Processes", John Wiley & Sons, 1984, 453 pages.

Verboekend et al., "Hierarchical Y and USY Zeolites Designed by Post-Synthetic Strategies", Adv. Funct. Mater., 22, (2012), pp. 916-928.

Chinese Office Action for Chinese Application No. 201880080349.7, dated Jul. 29, 2021 with translation, 12 pages.

Mazzotti, M., et al., "Robust Design of Countercurrent Adsorption Separation Process: 2. Multicomponent Systems," Nov. 1994, pp. 1825-1842, vol. 40(11). AIChE Journal.

Indian Examination Report for Indian Application No. 202017024115, dated Dec. 24, 2021, with translation, 6 pages.

Indian Examination Report for Indian Application No. 202017025692, dated Jan. 6, 2022, with translation, 5 pages.

ZEOLITE ADSORBENTS BASED ON BARIUM, STRONTIUM, POTASSIUM AND SODIUM, PREPARATION PROCESS THEREFOR, AND USES THEREOF

CROSS-REFERENCE TO RELATED APPLICATIONS

This is the national phase of International Application No. PCT/FR2018/053328, filed 17 Dec. 2018, which claims priority to French Application No. 1763033, filed 22 Dec. 2017. The disclosure of each of these applications is incorporated herein by reference in its entirety for all purposes.

TECHNICAL FIELD

The invention relates to adsorbents based on agglomerated crystals of zeolite X comprising barium, strontium and potassium, to the process for producing same and to the uses thereof.

These adsorbents can be used more particularly for the liquid-phase or gas-phase production of very pure para-xylene from a feedstock of aromatic hydrocarbons containing isomers comprising 8 carbon atoms.

PRIOR ART

It is known in the prior art that adsorbents comprising crystalline aluminosilicates can be used to separate certain hydrocarbons from mixtures containing them. In the field of the separation of aromatic hydrocarbons and in particular the separation of aromatic C8 isomers, it is generally acknowledged that the use of particular cations in the cationic sites of crystalline aluminosilicate zeolites improves the selectivity of the zeolite for one of the aromatic C8 isomers. This differential adsorption within the zeolite enables the separation of the various aromatic C8 isomers, which is used industrially for the production of very pure para-xylene from a feedstock of aromatic hydrocarbons containing isomers comprising 8 carbon atoms.

Thus, the use of zeolite adsorbents consisting of zeolites X or Y comprising, in addition to sodium cations, barium, potassium or strontium cations, alone or as mixtures, for selectively adsorbing para-xylene in the liquid phase in an aromatic hydrocarbon mixture, is well known in the prior art.

U.S. Pat. Nos. 3,558,730, 3,663,638 and 3,960,774 show that zeolite adsorbents comprising aluminosilicates of faujasite (FAU) structure based on sodium and barium or based on sodium, barium and potassium are effective for separating the para-xylene present in aromatic C8 fractions (fractions comprising aromatic hydrocarbons comprising 8 carbon atoms). The above adsorbents are preferably used as adsorption agents in liquid-phase processes, in particular of simulated counter-current type, similar to those described in U.S. Pat. No. 2,985,589 and which apply, inter alia, to aromatic C8 fractions.

U.S. Pat. Nos. 3,558,730, 3,626,020 and 3,997,620 show that zeolite adsorbents comprising aluminosilicates of faujasite (FAU) structure based on sodium and barium or based on sodium, barium and strontium are effective for separating the para-xylene present in aromatic C8 fractions (fractions comprising aromatic hydrocarbons comprising 8 carbon atoms).

However, in general, the adsorption properties of zeolites for aromatic hydrocarbons comprising 8 carbon atoms (xylenes and ethylbenzene) vary very finely as a function of the size and shape of the pores and also of the position of the cations within the structure which have an influence both on the electrostatic field present within the zeolite and on the form of the accessible volume in the pores. Other parameters, such as the polarizability of the cations and molecules or the flexibility of the structure, may also have an influence. It is therefore extremely difficult to predict theoretically and with accuracy the adsorption characteristics of a zeolite with respect to aromatic hydrocarbons comprising 8 carbon atoms.

To improve the adsorption selectivity of zeolites having the faujasite structure for aromatic C8 isomers, numerous studies have mentioned the influence of the Si/Al ratio of the zeolite, the nature of the exchange cations, and also the water content thereof. Similarly, it is very difficult to predict the degree of improvement because these factors exert combined actions on the adsorption characteristics of zeolites. In particular, it is difficult to predict the impact of the relative proportion of the cations chosen from sodium, barium, strontium and potassium in the case of a zeolite of faujasite (FAU) structure, and more specifically in the case of a zeolite of faujasite (FAU) structure of type X.

U.S. Pat. No. 3,997,620 presents agglomerates in which the agglomeration binder is not zeolitized, said agglomerates being exchanged with barium or with strontium, such that the Ba/Sr weight ratio is between 1:1 and 15:1. The examples of this patent show that the purity of the extract improved with the addition of strontium cations. However, the PX/MX and PX/OX selectivities are greatly decreased, which is problematic for the production of highly pure para-xylene.

The synthesis of the zeolites results in crystals (generally in powder form) the use of which on the industrial scale is particularly difficult (substantial losses of feeds during the manipulations). The agglomerated forms of these crystals are therefore preferred, in the form of grains, yarns and other agglomerates, these said forms possibly being obtained by extrusion, pelletizing, and other agglomeration techniques known to those skilled in the art. These agglomerates do not have the drawbacks inherent in pulverulent materials.

These agglomerates, whether they are in the form of platelets, beads, extrudates or the like, are generally formed from zeolite crystals, which constitute the active element (in the sense of adsorption) and of a binder intended to ensure cohesion of the crystals in the form of agglomerates and to give them sufficient mechanical strength to withstand vibrations and movements to which they are subjected during the operations for separation of the isomers of the aromatic C8 fractions. However, the adsorption properties of these agglomerates are obviously reduced relative to the crystal powder, because of the presence of agglomeration binder which is inert with respect to the adsorption. Various means have already been proposed for overcoming this drawback of the agglomeration binder being inert with respect to adsorption performance, among which is the conversion of all or at least part of the agglomeration binder into zeolite that is active from the point of view of adsorption. This operation is now well known to those skilled in the art, for example under the name "zeolitization". In order to perform this operation easily, use is made of zeolitizable binders, usually clays belonging to the kaolinite family, which have preferably been calcined beforehand at temperatures generally between 500° C. and 700° C.

Patent application FR 2 789 914 describes for example a process for producing zeolite X agglomerates, having an Si/Al ratio of between 1.15 and 1.5, containing barium and optionally potassium. The agglomerates thus obtained, after zeolitization of the binder, have, from the point of view of adsorption of para-xylene contained in the aromatic C8 fractions, improved properties relative to adsorbents prepared from the same amount of zeolite X and of binder, but the binder of which is not zeolitized.

The important factors which influence the performance levels of a process for separation by adsorption encompassing in particular the adsorption selectivity, the adsorption capacity and the matter transfer kinetics which define the rates of adsorption and desorption of the various compounds. The adsorbent must thus have good matter transfer properties in order to guarantee a sufficient number of theoretical plates to achieve efficient separation of the mixed species, as indicated by Ruthven in the book entitled "Principles of Adsorption and Adsorption Processes", John Wiley & Sons, (1984), pages 326 and 407. Ruthven indicates (ibid., page 243), that, in the case of an agglomerated adsorbent, the overall matter transfer depends on the addition of the intra-crystalline diffusional resistance and of the inter-crystalline diffusional resistance. The intra-crystalline diffusional resistance is proportional to the square of the radii of the crystals and inversely proportional to the diffusivity of the intra-crystalline molecules The inter-cystalline diffusional resistance (also called macroporous resistance) is for its part proportional to the square of the radii of the agglomerates and inversely proportional to the diffusivity of the molecules in the macropores. For a given zeolite structure, a given agglomerate size and a given operating temperature, the diffusivities are fixed, and the only means of improving the matter transfer consists in reducing the diameter of the crystals. A gain with regard to the overall transfer will thus be obtained by reducing the size of the crystals.

Consequently, those skilled in the art expect agglomerated zeolite adsorbents having both a good xylene adsorption capacity and a good selectivity for para-xylene to have very good xylene separation properties when they are produced from small zeolite crystals in liquid-phase processes for separating the para-xylene contained in aromatic C8 fractions, for example of simulated counter-current type. However, it is impossible for those skilled in the art to define a priori or theoretically and with accuracy the adsorption characteristics of a FAU zeolite, in particular of type X, comprising barium and potassium, and optionally other cations such as sodium and strontium, with respect to aromatic hydrocarbons comprising 8 carbon atoms.

Surprisingly, it appears that new adsorbents based on zeolite X comprising barium, potassium, strontium and sodium and having a specific barium, potassium, strontium and sodium composition, make it possible to concomitantly maximize the productivity and minimize the production costs of a process for separating the para-xylene contained in aromatic C8 fractions. The present invention also proposes a process for separating xylenes using an adsorbent based on zeolite X having a specific barium, potassium, strontium and sodium composition, allowing the production of highly pure para-xylene, with improved productivity, from a feedstock of aromatic hydrocarbons containing isomers comprising 8 carbon atoms.

SUMMARY OF THE INVENTION

The invention relates to a zeolite adsorbent comprising zeolite X crystals and comprising barium, potassium, strontium and sodium, in which the $K_2O/(K_2O+SrO+BaO+Na_2O)$ molar ratio of the species in oxide form is between 1.5% and 8.0%, preferably between 2.0% and 7.0%, and preferably between 2.5% and 6.0%, limits included. In one advantageous variant, the $K_2O/(K_2O+SrO+BaO+Na_2O)$ molar ratio of the species in oxide form is between 2.5% and 4.0%, for example equal to 3.0%. The $SrO/(K_2O+SrO+BaO+Na_2O)$ molar ratio of the species in oxide form is between 0.5% and 8.0%, preferably between 0.5% and 7.0%, very preferably between 1.0% and 6.0%, and even more preferably between 1.0% and 4.0%, limits included. In one advantageous variant, the $SrO/(K_2O+SrO+BaO+Na_2O)$ molar ratio of the species in oxide form is between 1.0% and 3.0%, for example 1.5%.

Preferably, the $SrO/K_2O$ molar ratio of the species in oxide form is between 0.3 and 2.0, preferably between 0.35 and 1.5, preferably between 0.4 and 1.0, limits included. In one advantageous variant, the $SrO/K_2O$ molar ratio of the species in oxide form is for example equal to 0.5.

The sodium oxide $Na_2O$ content is advantageously less than 0.3% by weight and preferably less than 0.2% by weight relative to the total mass of the adsorbent. The total content of alkali metal or alkaline-earth metal ion oxides other than barium oxide BaO, potassium oxide $K_2O$, strontium oxide SrO and sodium oxide $Na_2O$ is advantageously less than 1% by weight, preferably between 0% and 0.5% by weight, and very preferably between 0% and 0.3% by weight, limits included, relative to the total mass of the adsorbent.

The sum of the contents of barium oxide BaO, of potassium oxide $K_2O$, of strontium oxide SrO, of sodium oxide $Na_2O$ and of any other alkali metal or alkaline-earth metal oxides represents the total content in % by weight of the species in oxide form present in the adsorbent. The barium oxide content in % by weight relative to the total mass of the adsorbent can thus be calculated directly from the other contents of the species in oxide form in % by weight relative to the total mass of the adsorbent.

In the present invention, it should be understood that the weight contents expressed in weight of oxides are expressed relative to the total weight of the anhydrous adsorbent (weight corrected for the loss on ignition).

The zeolite X crystals advantageously have an Si/Al atomic ratio of between 1.00 and 1.50, preferably between 1.00 and 1.45, more preferably between 1.05 and 1.50, more preferentially between 1.05 and 1.45, and more preferably between 1.10 and 1.50, and even more preferably between 1.10 and 1.45, limits included.

The number-average diameter of the zeolite X crystals is advantageously less than or equal to 1.5 µm, preferably between 0.1 µm and 1.2 µm, more preferably between 0.1 µm and 1.0 µm, limits included.

The loss on ignition of the adsorbent according to the invention, measured at 950° C. according to standard NF EN 196-2, is advantageously between 4.0% and 7.7% and preferably between 4.5% and 6.5% and very preferably between 4.8% and 6.0% by weight, limits included.

The number-average diameter of the adsorbent according to the invention may be between 0.2 mm and 2.0 mm, in particular between 0.2 mm and 0.8 mm and preferably between 0.2 mm and 0.65 mm, limits included.

The invention also relates to a process for preparing an adsorbent as described above, comprising at least the steps of:

a) agglomeration of a powder of zeolite X crystals with a binder, and forming, then drying and calcining,
b) optional zeolitization of the binder,
c) simultaneous, sequential or alternating cation exchange of the agglomerate by bringing into contact with solutions containing barium ions, potassium ions or strontium ions alone or as a mixture, one or more times, then washing and drying of the agglomerate thus treated, and d) activation of the zeolite adsorbent thus obtained.

Preferably, the process for preparing the adsorbent implements a step b) of zeolitization of the binder.

Preferably, the solution(s) of barium ions, of strontium ions, of potassium ions of step c) have a concentration of between 0.5 and 2 M.

The invention also relates to an adsorbent as described above, which can be obtained according to the preparation process above. The invention also relates to the use of said adsorbent according to the invention in processes for:

separating fractions of aromatic C8 isomers and in particular xylenes,
separating isomers of substituted toluene, such as nitrotoluene, diethyltoluene, toluenediamine, or the like,
separating cresols,
separating polyhydric alcohols, and in particular for separating para-xylene from fractions of aromatic isomers comprising 8 carbon atoms.

The invention also relates to a process for recovering para-xylene from fractions of aromatic hydrocarbon isomers containing 8 carbon atoms, in the liquid phase, by adsorption of the para-xylene by means of said adsorbent according to the invention in the presence of a desorbent, preferably chosen from toluene and para-diethylbenzene.

Said process may be of simulated moving bed type, preferably in simulated counter-current mode.

The invention also relates to a process for recovering para-xylene from fractions of aromatic hydrocarbon isomers containing 8 carbon atoms, in the gas phase, by adsorption of the para-xylene by means of said adsorbent according to the invention in the presence of a desorbent, preferably chosen from toluene and para-diethylbenzene.

The invention also relates to a process for separating polyhydric alcohols using said adsorbent according to the invention.

The invention also relates to a process for separating isomers of substituted toluene, such as nitrotoluene, diethyltoluene or toluenediamine, using said adsorbent according to the invention.

The invention finally relates to a process for separating cresols using said adsorbent according to the invention.

In the text hereinbelow, unless otherwise indicated, the limits of a range of values are included in that range, especially in the expressions "between" and "ranging from . . . to . . . ".

DETAILED DESCRIPTION OF THE INVENTION

A first subject of the present invention is thus zeolite adsorbents based on zeolite X. These adsorbents are particularly suitable for use in a process for separating para-xylene in the liquid phase, preferably of simulated counter-current type.

Thus, the present invention relates to a zeolite adsorbent comprising zeolite X crystals and comprising barium, strontium, potassium and sodium, in which the $K_2O/(K_2O+SrO+BaO+Na_2O)$ molar ratio of the species in oxide form is between 1.5% and 8.0%, preferably between 2.0% and 7.0%, and preferably between 2.5% and 6.0%, limits included. In one advantageous variant, the $K_2O/(K_2O+SrO+BaO+Na_2O)$ molar ratio, expressed in terms of oxides, is between 2.5% and 4.0%, limits included, for example equal to 3.0%. The $SrO/(K_2O+SrO+BaO+Na_2O)$ molar ratio of the species in oxide form is between 0.5% and 8.0%, preferably between 0.5% and 7.0%, very preferably between 1.0% and 6.0%, and even more preferably between 1.0% and 4.0%, limits included. In one advantageous variant, the $SrO/(K_2O+SrO+BaO+Na_2O)$ molar ratio of the species in oxide form is between 1.0% and 3.0%, limits included, for example 1.5%.

Preferably, the $SrO/K_2O$ molar ratio of the species in oxide form is between 0.3 and 2.0, preferably between 0.35 and 1.5, preferably between 0.4 and 1.0, limits included. In one advantageous variant, the $SrO/K_2O$ molar ratio of the species in oxide form is for example equal to 0.5.

The adsorbents according to the invention may also comprise a non-zeolite phase, that is to say a non-crystalline phase which is essentially inert with respect to the adsorption. In the case where the adsorbent according to the invention comprises a non-zeolite phase, the $K_2O/(K_2O+SrO+BaO+Na_2O)$ molar ratio takes into account the oxides included in said non-zeolite phase.

The sodium oxide $Na_2O$ content in the adsorbent according to the invention is advantageously less than 0.3% by weight and preferably less than 0.3% by weight relative to the total mass of the adsorbent. The total content of alkali metal or alkaline-earth metal ion oxides other than barium oxide BaO, potassium oxide $K_2O$, strontium oxide SrO and sodium oxide $Na_2O$ in the adsorbent according to the invention is advantageously less than 1% by weight, preferably between 0% and 0.5% by weight, and very preferably between 0% and 0.3% by weight, limits included, relative to the total mass of the adsorbent.

The zeolite adsorbent according to the present invention is an adsorbent based on crystals of FAU zeolite of type X. the term "zeolite X" is intended to mean zeolites of which the Si/Al atomic ratio is between 1.00 and 1.50, limits included, preferably between 1.05 and 1.50, limits included, and even more preferably between 1.10 and 1.50, limits included.

Among the zeolites X, it is now commonly accepted to recognize two subgroups known as LSX zeolites and MSX zeolites. The LSX zeolites have an Si/Al atomic ratio equal to approximately 1 and the MSX zeolites have an Si/Al atomic ratio of between approximately 1.05 and approximately 1.15, limits included.

In the zeolite adsorbent of the present invention, and according to one preferred embodiment, the term "FAU zeolite of type X" is intended to mean the FAU zeolites of type X defined above, said zeolites being hierarchically porous, that is to say hierarchically porous zeolites of type X (or HPX), hierarchically porous zeolites of type MSX (or HPMSX) and hierarchically porous zeolites of type LSX (or HPLSX), and more particularly hierarchically porous FAU zeolites with an Si/Al atomic ratio of between 1.00 and 1.50, preferably between 1.00 and 1.45, more preferably between 1.05 and 1.50, more preferentially between 1.05 and 1.45, and even more preferably between 1.10 and 1.50 and even more preferably between 1.10 and 1.45, limits included.

The invention also comprises the zeolite adsorbents comprising mixtures of two or more hierarchically porous FAU zeolites as have just been defined.

The term "hierarchically porous zeolite" is intended to mean a zeolite which has both micropores and mesopores, in other words a zeolite which is both microporous and mesoporous. The term "mesoporous zeolite" is intended to mean a zeolite of which the microporous zeolite crystals have, together with the microporosity, internal cavities of nanometric size (mesoporosity), easily identifiable by observation using a transmission electron microscope (TEM), as described for example in U.S. Pat. No. 7,785,563: the observation by transmission electron microscopy (TEM) makes it possible to verify whether the zeolite crystals are solid zeolite crystals (i.e. non-mesoporous) or solid zeolite crystal aggregates or mesoporous crystals or mesoporous crystal aggregates.

The crystalline structure of the FAU zeolite of type X in the zeolite adsorbent in the present invention is identifiable by X-ray diffraction (known to those skilled in the art by the acronym XRD).

According to one preferred embodiment, the zeolite adsorbent has an Si/Al atomic ratio of between 1.00 and 2.00, preferably between 1.00 and 1.80, limits included, more preferably between 1.15 and 1.80, limits included, and even more preferably between 1.15 and 1.60, limits included.

In the present document, the term "number-average diameter" or else "size" is used for the zeolite crystals and for the zeolite agglomerates. The method of measurement of these parameters is explained below in the description. According to one preferred embodiment of the invention, the number-average diameter of the zeolite X crystals is less than or equal to 1.5 µm, preferably between 0.1 µm and 1.2 µm, more preferably between 0.1 µm and 1.0 µm, limits included.

The zeolite adsorbent of the invention is preferably in the form of an agglomerate, that is to say that it consists of crystals of zeolite(s) and of at least one non-zeolite phase which is an agglomeration binder allowing the cohesion of the crystals to one another. Thus, the zeolite adsorbent of the invention is often referred to as "agglomerate" in the present disclosure.

The mass fraction of zeolite X in the adsorbent according to the present invention may be at least 80% by weight of zeolite(s) X relative to the total weight of the anhydrous adsorbent, preferably at least 90%, this mass fraction possibly ranging up to 100% and typically up to 99.5% by weight.

According to one preferred embodiment, the zeolite adsorbent according to the invention has a loss on ignition, measured at 950° C. according to standard NF EN 196-2, of between 4.0% and 7.7%, preferably between 4.5% and 6.5% and advantageously between 4.8% and 6%, limits included.

The zeolite adsorbent according to the present invention preferentially has a mechanical strength generally greater than or equal to 1.8 MPa, typically greater than or equal to 2.1 MPa. This mechanical strength is measured by the Shell series SMS 1471-74 method adapted for agglomerates less than 1.6 mm in size.

The adsorption capacity is for its part measured by measuring the micropore volume of the adsorbent evaluated according to the Dubinin-Raduskevitch equation by adsorption of nitrogen ($N_2$) at a temperature of 77K, after degassing under vacuum at 300° C. for 16 hours. The micropore volume of the zeolite adsorbents of the invention was thus measured as being between 0.245 $cm^3/g$ and 0.300 $cm^3/g$, typically in a range from 0.250 $cm^3/g$ to 0.290 $cm^3/g$, limits included.

According to another aspect, the invention relates to a process for preparing the zeolite agglomerates as have just been defined, said process comprising at least the steps of
  a) agglomeration of a powder of zeolite X crystals with a binder, and forming, then drying and calcining,
  b) optional zeolitization of said binder, preferably by the action of an alkaline basic solution,
  c) cation exchange of the agglomerate by bringing into contact with solutions of barium ions, potassium ions or strontium ions. The potassium ion, strontium ion or barium ion concentrations in the solution are adjusted in order to reach the barium, potassium and strontium contents intended in the adsorbent and thus the intended $K_2O/(K_2O+SrO+BaO+Na_2O)$ and $SrO/(K_2O+SrO+BaO+Na_2O)$ molar ratios. The cation exchange of the agglomerate with barium, potassium and strontium may be carried out in a simultaneous, sequential or alternating manner by bringing into contact with solutions containing the barium ions, the potassium ions or the strontium ions alone or as a mixture of 2 or 3 ions. These operations may be carried out one or more times.

Between each exchange step, the solid is washed several times so as to remove from it the excess salt, and dried at the end of the various exchange steps,
  d) activation of the zeolite agglomerate.

Preferably, the process for preparing the zeolite agglomerates implements a step b) of zeolitization of the binder.

Preferably, the solution(s) of barium ions, of strontium ions, of potassium ions of step c) have a concentration of between 0.5 and 2 M.

The size of the zeolite X crystals used in step a) is measured by observation with a scanning electron microscope (SEM) or by observation with a transmission electron microscope (TEM). This SEM or TEM observation also makes it possible to confirm the presence of non-zeolite phase comprising for example the binder, or the residual binder not converted during the optional zeolitization step, or any other amorphous phase in the agglomerates.

According to one embodiment, the zeolite X used in step a) is a hierarchically porous FAU zeolite of type X. The crystals of hierarchically porous FAU zeolite of type X having a large external surface area may be obtained according to various methods known to those skilled in the art and for example according to the synthesis described by Inayat et al. (*Angew. Chem. Int. Ed.*, (2012), 51, 1962-1965).

It is also possible to prepare said crystals by synthesis by seeding and/or by adjusting the synthesis operating conditions such as the $SiO_2/Al_2O_3$ ratio, the sodium content and the alkalinity of the synthesis mixture or else according to processes for post-treatment of crystals of FAU zeolite of type X which are conventional and known to those skilled in the art.

The post-treatment processes generally consist in eliminating the atoms from the zeolite network already formed, either by one or more acid treatments which dealuminate the solid, said treatment(s) being followed by one or more wash(es) with sodium hydroxide (NaOH) in order to remove the aluminous residues formed as described for example by D. Verboekend et al. (*Adv. Funct. Mater.*, 22, (2012), pp. 916-928), or else by treatments which combine the action of an acid and that of a structuring agent which improve the efficiency of the acid treatment, as described for example in application WO 2013/106816.

The agglomeration and the forming (step a) can be carried out according to all of the techniques known to those skilled in the art, such as extrusion, compacting, agglomeration and the like. The proportions of optionally zeolitizable (see definition below) agglomeration binder and of zeolite(s) used are typically those of the prior art, that is to say from 5 parts to 20 parts by weight of binder per 95 parts to 80 parts by weight of zeolite. The agglomerates from step a), whether they are in the form of balls, extruded pieces or the like, generally have a number-average diameter (or their largest dimension when they are not spherical) of between 0.2 mm and 2 mm, and in particular of between 0.2 mm and 0.8 mm and preferably between 0.2 mm and 0.65 mm, limits included.

At the end of step a), the finest agglomerate particles can be removed by cycloning and/or sieving and/or the particles that are too coarse can be removed by sieving or crushing, in the case of extruded pieces, for example.

The agglomeration binder used in step a) may be zeolitizable. It then contains at least 80%, preferably at least 90%, more preferably at least 95%, more particularly at least 96%, by weight, of zeolitizable clay and may also contain other mineral binders such as bentonite, attapulgite, and the like. The term "zeolitizable clay" is intended to mean a clay or a mixture of claims which are capable of being converted into zeolite matter (i.e. active matter in the sense of the adsorption), usually by the action of an alkaline basic solution. The zeolitizable clay belongs in general to the family of kaolins, kaolinites, nacrites, dickites, hallyosite and/or metakaolins. Kaolin is preferred and is the most commonly used.

Other clays, such as in particular sepiolite or attapulgite, may also be used.

In any event, the clays may be used in their crude form or may be subjected beforehand to one or more treatments, for example chosen from calcining, acid treatment, chemical modification, and the like.

The zeolite X powder used in step a) may result from the synthesis of zeolite X crystals comprising predominantly, or even exclusively, sodium cations, for example NaX zeolites, but the use of a powder which has undergone one or more cation exchanges, after it has been synthesized and before it has been used in step a), would not depart from the context of the invention.

During step a), in addition to the zeolite X powder and the binder, one or more additives may also be added, for example additives intended to facilitate the agglomeration or to improve the hardening of the agglomerates formed, such as lignin, starch, carboxymethylcellulose, and other additives known to those skilled in the art. Silica may also be added. The optional source of silica may be of any type known to those skilled in the art, who are specialists in zeolite synthesis, for example colloidal silica, diatoms, perlite, fly ash, sand, or any other form of solid silica.

After the drying in step a), the calcining is carried out at a temperature generally between 500° C. and 700° C. In the case where the forming is carried out with a zeolitizable clay, this step makes it possible to convert the zeolitizable clay, typically kaolin, into metakaolin which can later be converted into zeolite during the zeolitization step (step b)). The principal thereof is set out in "Zeolite Molecular Sieves" by D. W. Breck, John Wiley and Sons, New York, (1973), p. 314-315.

The zeolitization of the agglomeration binder is performed according to any method known to those skilled in the art and can for example be carried out by immersing the product of step a) in an alkaline basic solution, which is generally aqueous, for example an aqueous solution of sodium hydroxide and/or of potassium hydroxide.

As a general rule, the concentration of the alkaline zeolitization solution is preferably between 0.5 M and 5 M, more particularly between 0.5 and 2 M. The zeolitization is preferably carried out hot, at a temperature above ambient temperature, and typically at temperatures of about from 80° C. to 100° C., for example between ambient temperature (i.e. approximately 20° C.) and the boiling point of the alkaline zeolitization solution. The duration of the zeolitization process is generally between a few tens of minutes and a few hours, preferably between approximately 1 hour and 8 hours.

The step c) of exchange of the cations of the zeolite X with barium and/or strontium and/or potassium is carried out according to the conventional methods known to those skilled in the art, and usually by bringing the agglomerates resulting from step a) or from step b) into contact with a salt, such as a barium chloride ($BaCl_2$) for exchange with barium and/or strontium chloride ($SrCl_2$) for exchange with strontium and/or potassium chloride (KCl) for exchange with potassium, in aqueous solution at a temperature of between ambient temperature and 100° C., and preferably of between 80° C. and 100° C. In order to rapidly obtain low sodium oxide contents, i.e. of less than 1%, it is preferable to carry out the process with a large excess of barium and/or strontium and/or potassium ions relative to the cations of the zeolite that it is desired to exchange, typically an excess of around 10 to 12, advantageously by performing successive exchanges. Preferably, the solution(s) of barium ions, of strontium ions, of potassium ions of step c) have a concentration of between 0.5 and 2 M.

As previously indicated, it is also possible to agglomerate, in step a), zeolite X powder already containing potassium ions (pre-exchange of the cations present in the starting zeolite X, typically sodium cations, with potassium ions before step a)) and possibly dispense with potassium exchanges during step c).

Washing, generally and preferably with water, followed by drying of the agglomerate thus obtained, is then carried out.

The activation which follows the drying is carried out conventionally, according to methods known to those skilled in the art, for example at a temperature generally between 100° C. and 400° C., preferably between 200° C. and 300° C. The objective of this activation step d) is to fix the water content, and also the loss on ignition of the adsorbent in a manner that is optimal for the envisaged use. The general procedure is a thermal activation, which is performed preferentially at between 200° C. and 300° C. for a certain time depending on the desired water content and desired loss on ignition, typically from 1 to 6 hours.

The present invention also relates to the uses of the zeolite adsorbents described above as adsorption agents capable of advantageously replacing the adsorption agents described in the literature for the uses listed below:
  separating fractions of aromatic C8 isomers and in particular xylenes,
  separating isomers of substituted toluene, such as nitrotoluene, diethyltoluene, toluenediamine, or the like,
  separating cresols,
  separating polyhydric alcohols, such as sugars.

The invention relates in particular to a process for recovering highly pure para-xylene from fractions of aromatic isomers comprising 8 carbon atoms, consisting in using, as adsorption agent for the para-xylene, a zeolite adsorbent according to the invention, used in liquid-phase but also gas-phase processes. The term "highly pure para-xylene" is intended to mean a product suitable for use in the production of terephthalic acid or dimethyl terephthalate, that is to say with a purity of at least 99.5% by weight, preferably at least 99.7% by weight, preferably at least 99.8% by weight and even more preferably at least 99.9% by weight. The purity of the para-xylene can be determined by chromatographic methods. A gas chromatography method that can be used for determining both the purity of the para-xylene and the specific amounts of impurities is the ASTM D-3798 method.

It is thus possible to separate the desired product (para-xylene) by (batchwise) preparative adsorption liquid chromatography, and advantageously continuously in a simulated moving bed, that is to say in simulated counter-current or simulated co-current mode, and more particularly in simulated counter-current mode.

The process for recovering para-xylene according to the invention using the adsorbent described according to the present invention has the advantage of maximizing the productivity but also minimizing the operating costs of the process, that is to say both maximizing the flow of feedstock to be treated and minimizing the flow of desorbent required. This is particularly true under the following operating conditions for an industrial adsorption unit of simulated counter-current type:

number of beds: 6 to 30,
number of zones: at least 4 operating zones, each being located between a feed point and a drawing off point,
temperature between 100° C. and 250° C., preferably between 150° C. and 190° C.,
pressure of the industrial unit between the xylene bubble-point pressure at the temperature of the process and 3 MPa,
ratio of desorbent/feedstock flow rates between 0.7 and 2.5, for example between 0.9 1.8, for a single (stand-alone) adsorption unit and between 0.7 and 1.4 for an adsorption unit combined with a crystallization unit,
recycling ratio (i.e. ratio of the average recycling flow rate (average flow rate of zones, weighted with respect to the number of beds per zone) to the feed flow rate) between 2.5 and 12, preferably between 3.5 and 6.

The invention also relates to a process for recovering para-xylene from fractions of aromatic hydrocarbon isomers containing 8 carbon atoms, in the liquid phase, by adsorption of the para-xylene, comprising the following successive steps:

a) a step of bringing the feedstock into contact with a bed of adsorbent comprising at least one zeolite adsorbent as defined above,
b) a step of bringing the bed of adsorbent into contact with a desorbent, preferably chosen from toluene and para-diethylbenzene.

The process for recovering para-xylene may be of simulated moving bed type, preferably in simulated counter-current mode The invention also relates to a process for recovering para-xylene from fractions of aromatic hydrocarbon isomers containing 8 carbon atoms, in the gas phase, by adsorption of the para-xylene by means of an adsorbent as defined above, comprising the following successive steps:

a) a step of bringing the feedstock into contact with a bed of adsorbent comprising at least one zeolite adsorbent as defined above,
b) a step of bringing the bed of adsorbent into contact with a desorbent, preferably chosen from toluene and para-diethylbenzene.

In one variant, the process for separating highly pure para-xylene is carried out in a simulated moving bed starting from a feedstock of aromatic hydrocarbons containing isomers comprising 8 carbon atoms, comprising the following steps:

a) a step of bringing the feedstock into contact with a bed of adsorbent comprising at least one zeolite adsorbent as defined above, in such a way as to preferentially adsorb the para-xylene,
b) a step of bringing the bed of adsorbent into contact with a desorbent, the desorbent preferentially being either toluene or para-diethylbenzene,
c) a step of drawing off, from the bed of adsorbent, a stream containing the desorbent and the least selectively adsorbed feedstock products,
d) a step of drawing off, from the bed of adsorbent, a stream containing the desorbent and the desired product, namely the para-xylene,
e) a separation of the stream resulting from step c) into a first stream containing the desorbent and a stream string containing the least selectively adsorbed feedstock products,
f) a separation of the stream resulting from step d) in a first stream containing the desorbent and a second stream containing para-xylene with a level of purity greater than or equal to 90%, preferably greater than or equal to 99%, and very preferably greater than or equal to 99.7%.

In this respect, reference may be made to the teaching of U.S. Pat. Nos. 2,985,589, 5,284,992 and 5,629,467.

Operating conditions of an industrial simulated co-current adsorption unit are generally the same as those which operate in simulated counter-current mode, with the exception of the recycling ratio which is generally between 0.8 and 7. In this respect, reference may be made to U.S. Pat. Nos. 4,402,832 and 4,498,991.

The desorption solvent may be any desorbent known to those skilled in the art and the boiling point of which is below that of the feedstock, such as toluene, but also a desorbent of which the boiling point is above that of the feedstock, such as para-diethylbenzene (PDEB). Selectivity of the adsorbents according to the invention for the adsorption of para-xylene contained in C8 aromatic fractions is optimal when the loss on ignition thereof, measured at 950° C., is generally between 4.0% and 7.7%, preferably between 4.5% and 6.5%, and very preferably between 4.8% and 6.0%, limits included.

The invention also relates to a process for separating polyhydric alcohols, comprising a step of bringing the polyhydric alcohols into contact with an adsorbent as defined above.

The invention also relates to a process for separating isomers of substituted toluene, such as nitrotoluene, diethyltoluene or toluenediamine, comprising a step of bringing the isomers of substituted toluene into contact with an adsorbent as defined above.

The invention also relates to a process for separating cresols, comprising a step of bringing the cresols into contact with an adsorbent as defined above.

Characterization Techniques

Crystal Particle Size:

The number-average diameter of the zeolite X crystals used in step a) and of the crystals of zeolite X contained in the agglomerates is estimated by observation with a scanning electron microscope (SEM) or by observation with a transmission electron microscope (TEM).

In order to estimate the size of the zeolite crystals on the samples, a set of images is taken at a magnification of at least 5000. The diameter of at least 200 crystals is then measured using dedicated software, for example the Smile View software published by LoGraMi. The accuracy is of the order of 3%.

Chemical Analysis of the Zeolite Adsorbents—Si/Al Ratios and Oxide Contents

An elemental chemical analysis of the final product obtained at the end of steps a) to d) described above can be carried out according to various analytical techniques known to those skilled in the art. Among these techniques, mention may be made of the technique of chemical analysis by x-ray fluorescence as described in standard NF EN ISO 12677: 2011 on a wavelength-dispersive spectrometer (WDXRF), for example the Tiger S8 machine from the company Bruker.

X-ray fluorescence is a non-destructive spectral technique which exploits the photoluminescence of atoms in the X-ray range, to establish the elemental composition of a sample. Excitation of the atoms, generally with an X-ray beam or by electron bombardment, generates specific radiations after return to the ground state of the atom. The X-ray fluorescence spectrum has the advantage of depending very little on the chemical combination of the element, which offers a precise determination, both quantitatively and qualitatively. A measurement uncertainty of less than 0.4% by weight is conventionally obtained after calibration for each oxide. In the present invention, the barium, strontium, potassium, silicon and aluminium contents are preferably measured by the X-ray fluorescence method described above.

On the other hand, for the elements that are lighter in terms of atomic weight, such as sodium, and that are present in the adsorbent, inductively coupled plasma-optical emission spectroscopy (ICP-OES) according to standard UOP 961-12 is preferred in order to obtain greater accuracy.

ICP is a method of analysis by atomic emission spectroscopy, the source of which is a plasma generated by inductive coupling. In the present invention, the sodium contents are preferably measured by the ICP method according to standard UOP 961-12. In this case, an uncertainty with regard to the measurement below 0.01% for the sodium oxide weight content in the adsorbent is obtained for sodium.

These elemental chemical analyses make it possible both to verify the Si/Al atomic ratio of the zeolite within the agglomerate, and to verify the quality of the ion exchange described in step c). In the description of the present invention, the measurement uncertainty for the Si/Al atomic ratio is 0.05%.

The quality of the ion exchange is linked to the number of moles of sodium oxide, $Na_2O$, remaining in the zeolite agglomerate after exchange. More specifically, the degree of exchange with barium ions is determined by the ratio between the number of moles of barium oxide, BaO, and the number of moles of the combination ($BaO+K_2O+SrO+Na_2O$). Likewise, the degree of exchange with potassium and strontium ions is determined, respectively, by the ratio between the number of moles of potassium oxide, $K_2O$, and the number of moles of the combination ($BaO+K_2O+SrO+Na_2O$) or by the ratio between the number of moles of strontium oxide, SrO, and the number of moles of the combination ($BaO+K_2O+SrO+Na_2O$). BaO, $K_2O$, SrO and $Na_2O$ are expressed in the form of oxides. The total degree of exchange with barium, potassium and strontium ions is estimated from the sum of the three degrees of exchange previously described, corresponding to the ratio between the sum of the number of moles of barium oxide, of potassium oxide and of strontium oxide ($BaO+K_2O+SrO$) and the number of moles of the combination ($BaO+K_2O+SrO+Na_2O$). It should be noted that the contents of various oxides are given as percentage by weight relative to the total weight of the anhydrous zeolite adsorbent. In the description of the present invention, the measurement uncertainty with regard to the $K_2O/(K_2O+BaO+SrO+Na_2O)$ molar ratio is 0.3%, and the measurement uncertainty with regard to the $SrO/(K_2O+SrO+BaO+Na_2O)$ molar ratio is 0.3%.

Zeolite Adsorbent Particle Size:

The number-average diameter of the zeolite adsorbents obtained at the end of agglomeration and forming step a) is determined by analysis of the particle size distribution of a sample of agglomerate by imaging according to standard ISO 13322-2:2006, using a conveyor belt which allows the sample to pass in front of the camera lens.

The number-average diameter is then calculated from the particle size distribution by applying standard ISO 9276-2: 2001. In the present document, the term "number-average diameter" or else "size" is used for the zeolite agglomerates. The accuracy is about 0.01 mm for the size range of agglomerates of the invention.

Zeolite Adsorbent Mechanical Strength:

The technique for characterizing the mechanical strength representative of the crushing of the adsorbent in a bed or a reactor is the bulk mechanical strength characterization technique, as described in the Shell Method Series SMS 1471-74 (Shell Method Series SMS1471-74 Determination of Bulk Crushing Strength of Catalysts. Compression-Sieve Method), associated with the "BCS Tester" machine sold by the company Vinci Technologies. This method, initially intended for the characterization of catalysts of 3 to 6 mm, is based on the use of a 425 µm sieve which will make it possible in particular to separate the fines created during the crushing. The use of a 425 µm sieve remains suitable for particles with a diameter greater than 1.6 mm, but must be adapted according to the particle size of the zeolite adsorbents that it is desired to characterize. Standard ASTM D7084-04, which also describes a method for measuring the bulk crush strength of catalysts ("Determination of Bulk Crush Strength of Catalysts and Catalyst Carriers"), defines the through-size of the sieve to be used as being equal to half the diameter of the particles of catalysts to be characterized. The method provides for a preliminary step of sieving the sample of catalysts or adsorbents to be characterized. If an amount equal to 10% by weight of the sample passes through the screen, a sieve with a smaller through-size will be used The agglomerates of the present invention, generally in the form of balls or extrudates, in general have a number-average diameter or a length, i.e. largest dimension in the case of non-spherical agglomerates, of between 0.2 mm and 2 mm and in particular of between 0.2 mm and 0.8 mm and preferably between 0.2 mm and 0.65 mm. Consequently, a sieve that is adapted such that less than 10% by weight of the sample passes through the screen during a prior sieving step is used in place of the 425 µm sieve mentioned in the Shell SMS1471-74 standard method.

The measurement protocol is the following: a 20 $cm^3$ sample of agglomerated adsorbents pre-sieved with the appropriate sieve and pre-dried in an oven for at least 2 hours at 250° C. (instead of 300° C. mentioned in the Shell SMS1471-74 standard method), is placed in a metal cylinder with a known internal cross-section. An increasing force is applied stepwise to this sample by means of a piston, through a bed of 5 $cm^3$ of stainless steel balls in order to give a better distribution of the force exerted by the piston on the agglomerates of adsorbents (use of balls 2 mm in diameter for spherically shaped particles with a diameter strictly less than 1.6 mm). The fines obtained at the various pressure steps are separated by sieving (with appropriate sieve) and weighed.

The bulk crush strength is determined by the pressure in megapascals (MPa) for which the amount of accumulated fines passing through the sieve comes to 0.5% by weight of the sample. This value is obtained by plotting, on a graph, the mass of fines obtained as a function of the force applied to the bed of adsorbent and by interpolating with respect to 0.5% by mass of the accumulated fines. The mechanical bulk crush strength is typically between a few hundred kPa and a few tens of MPa and is generally between 0.3 MPa and 4 MPa. The precision is conventionally less than 0.1 MPa Determination of the Zeolite Fractions of the Zeolite Adsorbents:

The nature and amount of the various zeolite fractions are determined by x-ray diffraction analysis, known to those skilled in the art by the acronym XRD. This analysis is performed on a Bruker brand machine, and the amount of the zeolite fractions is then evaluated using the TOPAS software from the company Bruker.

Micropore Volume:

The crystallinity of the agglomerates is also evaluated by measuring their micropore volume while comparing it to that of a suitable reference (zeolite that is 100% crystalline under identical cationic treatment conditions or theoretical zeolite). This micropore volume is determined from the measurement of the adsorption isotherm of gas, such as nitrogen, at its liquefaction temperature. Prior to the adsorption, the zeolite-based adsorbent is degassed at between 300° C.-450° C. for a time of from 9 hours to 16 hours, under vacuum ($P<6.7\times10^{-4}$ Pa). Measurement of the nitrogen adsorption isotherm at 77K is then performed on a machine of ASAP 2010 M type from Micromeritics, taking at least 35 measurement points at relative pressures of ratio $P/P_0$ between 0.002 and 1. The micropore volume is determined according to Dubinin and Raduskevitch from the isotherm obtained, by applying standard ISO 15901-3:2007. The micropore volume evaluated according to Dubinin and Raduskevitch is expressed in $cm^3$ of liquid adsorbate per gram of adsorbent. The measurement uncertainty is ±0.003.

Loss on Ignition of the Zeolite Adsorbents:

The loss on ignition is determined under an oxidizing atmosphere, by calcination of the sample in air at a temperature of 950° C.±25° C., as described in standard NF EN 196-2 (April 2006). The measurement standard deviation is less than 0.1%.

Characterization of the Adsorption in Liquid Phase by Breakthrough:

The technique used to characterize the adsorption of molecules in liquid phase on a porous solid is the "breakthrough" technique, described by Ruthven in "Principles of Adsorption and Adsorption Processes" (Chapters 8 and 9, John Wiley & Sons, 1984) which defines the breakthrough curves technique as the study of the response to the injection of a scale of adsorbable constituents. The analysis of the mean exit time (first moment) of the breakthrough curves provides information on the amounts adsorbed and also makes it possible to evaluate the selectivities, that is to say the separation factor, between two adsorbable constituents. The injection of a non-adsorbable constituent used as tracer is recommended for estimating the non-selective volumes. The analysis of the dispersion (second moment) of the breakthrough curves makes it possible to evaluate the equivalent height of theoretical plates, based on the representation of a column by a finite number of hypothetical reactors that are ideally stirred (theoretical stages), which is a direct measurement of the axial dispersion and of the resistance to material transfer of the system.

EXAMPLES

Preparation of the Adsorbent Zeolites

A homogeneous mixture is prepared and 800 g of zeolite NaX crystals are agglomerated according to the procedure described in patent application FR2 999 098 (synthesis of example B) with 105 g of kaolin (expressed in calcined equivalent) and 45 g of colloidal silica sold under the trade name Klebosol®30 (containing 30% by weight of $SiO_2$ and 0.5% of $Na_2O$) with the amount of water which allows extrusion of the mixture. The extrudates are dried, crushed in such a way as to recover the grains of which the number-average diameter is equal to 0.7 mm, then calcined at 550° C. under a nitrogen stream for 2 hours.

200 g of agglomerates obtained are placed in a glass reactor equipped with a jacket regulated at a temperature of 100° C.±1° C., then 1.5 l of an aqueous sodium hydroxide solution having a concentration of 2.5 M are added and the reaction medium is left to stir for a period of 4 hours.

The agglomerates are then washed in water in 3 successive washing operations, followed by emptying of the reactor. The washing is known to have been efficient when the final pH of the washing waters measured is between 10.0 and 10.5.

Example 1: Cation Exchange with Barium, Potassium and Strontium

The sodium cations of the agglomerates obtained are exchanged with barium, potassium and strontium ions by means of an aqueous solution at 0.5 M of potassium chloride, of strontium chloride and of barium chloride at 95° C. in 4 stages. The potassium chloride, strontium chloride and barium chloride concentrations in the solution are adjusted in order to reach the barium, potassium and strontium contents intended in the adsorbent and thus the intended $K_2O/(K_2O+SrO+BaO+Na_2O)$ and $SrO/(K_2O+SrO+BaO+Na_2O)$ molar ratios. At each step, the volume of solution to mass of solid ratio is 20 ml/g and the exchange is continued for 3 hours each time. Between each exchange, the solid is washed several times so as to remove the excess salt therefrom. The agglomerates are then dried at 80° C. for 2 hours and, finally, activated at 250° C. for 2 hours under a nitrogen stream The loss on ignition measured, as described above, is 5.6%±0.1% for each sample. The degree of barium+potassium+strontium exchange of the agglomerates, calculated from the elemental analyses of the barium oxide, potassium oxide, strontium oxide and sodium oxide by X-ray fluorescence and ICP as described in the characterization techniques, is 99.7±0.2%.

Example 2: Breakthrough Test

A breakthrough test (frontal chromatography) is then carried out on the agglomerates obtained in Example 1 in order to evaluate their efficiency. The amount of adsorbent used for this test is approximately 30 g.

The procedure for obtaining the breakthrough curves is the following:

Filling the column with the sieve and placing in the test bench.

Filling with a solvent (toluene) at ambient temperature.

Gradual increase to the adsorption temperature under a stream of solvent (2 $cm^3$/min).

Injection of solvent at 2 $cm^3$/min when the adsorption temperature is reached.

Solvent/feedstock permutation to inject the feedstock (2 $cm^3$/min).

Injection of the feedstock is then maintained for a time sufficient to reach thermodynamic equilibrium.

Collection of the breakthrough product in a single flask then analysis of the composition of the product by GC The pressure is sufficient for the feedstock to remain in the liquid phase, i.e. 1 MPa. The adsorption temperature is 175° C. The composition of the feedstock used for the tests is the following:

a. Para-xylene: 18% by weight
b. Meta-xylene: 18% by weight
c. Ortho-xylene: 18% by weight
d. Ethylbenzene: 18% by weight
e. Para-diethylbenzene: 18% by weight
f. Isooctane: 10% by weight (this is used as a tracer for estimating the non-selective volumes and is not involved in the separation).

The binary selectivities of the compounds in pairs, denoted binary selectivities $\alpha_{i/k}$, are calculated from the adsorbed amounts $q_i$ and $q_k$ of the compounds i and k, the latter being determined by the material balance from the analysis of the composition of the breakthrough product and of the composition of the feedstock (in which feedstock the mass fraction of the compounds i and k is $y_i$ and $y_k$):

$$\alpha_{i/k} = \frac{q_i y_k}{q_k y_i}$$

The evaluation of the potential of these adsorbents during the simulated counter-current implementation is carried out on the basis of the equilibrium theory applied to multicomponent systems with constant selectivities, as described by Mazotti, Storti and Morbidelli in Robust Design of Countercurrent Adsorption Separation Processes: 2. Multicomponent Systems, AIChE Journal November 1994 Vol. 40, No. 11. In particular, reference is made in this case to equation 8, which describes the conditions to be met with regard to the reduced flow rates $m_j$ of the 4 sections (j=1 to 4) of a counter-current separation unit as represented diagrammatically in FIG. 1 of the article cited, in order to obtain complete separation.

$$\text{Section 1: } K_{ss} < m_1 \delta_1 < +\infty \qquad (8)$$
$$\text{Section 2: } K_{wk} < m_2 \delta_2 < K_{sk}$$
$$\text{Section 3: } K_{wk} < m_3 \delta_3 < K_{sk}$$
$$\text{Section 4: } -\frac{\epsilon_4 \delta_4}{\sigma(1-\epsilon_p)} < m_4 \delta_4 < K_{ww}.$$

This equation 8 refers to the adsorptivities $K_i$ of the various constituents, and also to the parameter $\delta_j$ of each section j defined by equation 7:

$$\delta_j = \sum_{l=1}^{NC} K_l y_l / (j=1,\ldots,4). \qquad (7)$$

It should be noted here that, by definition, the binary selectivity $\alpha_{i/k}$ between the compounds i and k is equal to the ratio of the adsorptivities $K_i/K_k$.

The reduced flow rate of each section of the unit is defined as being the ratio of the flow rate of the liquid phase to the flow rate of the adsorbed phase. Equation 8 indicates which are the limit reduced flow rates for each section. In a 4-section counter-current separation unit, the feedstock flow rate corresponds to the difference between the flow rate in zone 3 and the flow rate in zone 2, and the desorbent flow rate corresponds to the difference between the flow rate in zone 1 and the flow rate in zone 4.

Consequently, when it is desired to evaluate the maximum productivity which can be achieved with a given adsorbent, it is sought to evaluate the maximum amount of feedstock, but also to minimize the operating costs. An effective adsorbent is that which makes it possible both to maximize the flow rate of feedstock to be treated and to minimize the flow rate of desorbant required.

In order to determine the maximum amount of feedstock that can be treated, the difference between the maximum flow rate in zone 3 and the minimum flow rate in zone 2 is evaluated. It is possible to compare the performance levels in terms of maximum productivity of two adsorbents by comparing their maximum reduced flow rate of feedstock determined from the reduced flow rates of zones 2 and 3, respectively $m_2$ and $m_3$, according to the relationship: max $(m_{Feedstock})$=max$(m_3)$-min$(m_2)$.

If a constant-selectivity system is considered, the composition of the liquid phase which gives the highest stress in zone 2 and in zone 3 is the composition of the liquid phase at the point of injection of the feedstock into the unit. Indeed, starting from this point, the concentration of para-xylene, which is the compound most adsorbed, increases in the direction of circulation of the solid in zone 2 and decreases in the direction of circulation of the liquid in zone 3. The composition at this point can be approximated to the composition of the feedstock to be treated, and it is this composition that will be used to evaluate the term $\delta_2$ and $\delta_3$ of equation 8; the terms $\delta_2$ and $\delta_3$ being defined by equation 7 mentioned above.

For each adsorbent, this reduced flow rate max $(m_{Feedstock})$ is calculated from the values of binary selectivities measured experimentally.

In order to determine the minimum amount of desorbent to be injected, the difference between the minimum flow rate in zone 1 and the maximum flow rate in zone 4 is evaluated. It will be possible to compare the performance levels in terms of regeneratability of two adsorbents by comparing their minimum reduced flow rate of desorbent determined from the reduced flow rates of zones 1 and 4, respectively $m_1$ and $m_4$, according to the relationship: min$(m_{Des})$=min$(m_1)$-max$(m_4)$.

For a constant-selectivity system, the composition of the liquid phase which gives the highest stress in zone 1 and in zone 4 is the composition of the liquid phase at the point of injection of the desorbent into the unit. At this point, the liquid phase essentially contains desorbent. Its composition is used to evaluate the terms $\delta_1$ and $\delta_4$ of equation 8; the terms $\delta_1$ and $\delta_4$ being defined by equation 7 mentioned above.

For each adsorbent, the reduced flow rate min $(m_{Des})$ is calculated from the values of binary selectivities measured experimentally.

The ratio between max$(m_{feedstock})$ and min$(m_{Des})$ makes it possible to indicate the ability of the adsorbent to jointly maximize the productivity and minimize the operation costs of the process for separating para-xylene contained in the aromatic C8 fractions.

Table 1 makes it possible to compare the ratio of reduced flow rates between max$(m_{Feedstock})$ and min$(m_{Des})$ for various formulations of adsorbents having various molar ratios of the species in oxide form $K_2O/(K_2O+SrO+BaO+Na_2O)$ and $SrO/(K_2O+SrO+BaO+Na_2O)$. The $SrO/K_2O$ molar ratio of the species in oxide form is also indicated.

| Formulation | $K_2O/(K_2O + SrO + BaO + Na_2O)$ | $SrO/(K_2O + SrO + BaO + Na_2O)$ | $SrO/K_2O$ | $max(m_{Feedstock})/min(m_{Des})$ |
|---|---|---|---|---|
| A (not in accordance) | 0 | 0 | — | 0.84 |
| B (not in accordance) | 3 | 0 | — | 0.88 |
| C (not in accordance) | 5 | 0 | 0 | 0.89 |
| D (not in accordance) | 0 | 3 | — | 0.86 |
| E (not in accordance) | 0 | 5 | — | 0.82 |
| F (not in accordance) | 3 | 8.2 | 2.73 | 0.63 |
| G | 3 | 2 | 0.66 | 0.99 |
| H | 3.5 | 1.5 | 0.42 | 1.01 |
| I | 1.8 | 0.75 | 0.42 | 1.05 |

It is noted that the adsorbents G, H and I, which have a controlled strontium and potassium content compared with all of the cations in accordance with the invention, make it possible to obtain optimal ratios between $max(m_{feedstock})$ and $min(m_{Des})$.

On the other hand, the adsorbents A, B, D and F have contents which are not in accordance with the invention, resulting in the obtaining of degraded values for the ratio between $max(m_{feedstock})$ and $min(m_{Des})$.

This demonstrates the beneficial effect of the use of the Sr and K contents described in the invention.

The invention claimed is:

1. Zeolite adsorbent comprising zeolite X crystals and comprising barium, potassium, strontium and sodium, in which the $K_2O/(K_2O+SrO+BaO+Na_2O)$ molar ratio of the species in oxide form is between 0.015 and 0.08, limits included, and the $SrO/(K_2O+SrO+BaO+Na_2O)$ molar ratio of the species in oxide form is between 0.005 and 0.08, limits included.

2. Adsorbent according to claim 1, in which the $K_2O/(K_2O+SrO+BaO+Na_2O)$ molar ratio of the species in oxide form is between 0.02 and 0.07, limits included.

3. Adsorbent according to claim 1, in which the $SrO/(K_2O+SrO+BaO+Na_2O)$ molar ratio of the species in oxide form is between 0.005 and 0.07, limits included.

4. Adsorbent according to claim 1, in which the $SrO/K_2O$ molar ratio of the species in oxide form is between 0.3 and 2.0, limits included.

5. Adsorbent according to claim 1, also comprising a non-zeolite phase.

6. Adsorbent according to claim 1, in which the content of sodium oxide $Na_2O$ is less than 0.3% by weight relative to the total mass of the adsorbent.

7. Adsorbent according to claim 1, in which the total content of alkali metal or alkaline-earth metal ion oxides other than barium oxide BaO, potassium oxide $K_2O$, strontium oxide SrO and sodium oxide $Na_2O$ is less than 1% by weight, limits included, relative to the total mass of the adsorbent.

8. Adsorbent according to claim 1, in which the zeolite X crystals have an Si/Al atomic ratio of between 1.00 and 1.50, limits included.

9. Adsorbent according to claim 1, said adsorbent having a number-average diameter of between 0.2 mm and 2 mm, limits included.

10. Adsorbent according to one claim 1, in which the number-average diameter of the zeolite X crystals is less than or equal to 1.5 µm, limits included.

11. Adsorbent according to claim 1, having a loss on ignition, measured at 950° C. according to standard NF EN 196-2, of between 4.0 and 7.7% by weight.

12. Adsorbent according to claim 1, in which the mass fraction of zeolite X is at least 80% by weight of zeolite(s) X relative to the total mass of the adsorbent.

13. Process for preparing an adsorbent according to claim 1, comprising at least the following steps:
   a) agglomeration of a powder of zeolite NaX crystals with a binder, and forming, then drying and calcining,
   b) optional zeolitization of the binder,
   c) simultaneous, sequential or alternating cation exchange of the agglomerate by bringing into contact with solutions containing barium ions, potassium ions or strontium ions alone or as a mixture, one or more times, then washing and drying of the agglomerate thus treated, and
   d) activation of the zeolite adsorbent thus obtained.

14. Process according to claim 13, wherein the binder used in step a) contains at least 80% by weight of zeolitizable clay, and a source of silica, and in that the process comprises a step b) of zeolitization of the zeolitizable binder by action of an alkaline basic solution for a period of between a few tens of minutes and a few hours.

15. Adsorbent obtained according to the process of claim 13.

16. Process for recovering para-xylene from a feedstock comprising fractions of aromatic hydrocarbon isomers containing 8 carbon atoms, in the liquid phase, by adsorption of the para-xylene, comprising the following successive steps:
   a) bringing a feedstock into contact with a bed of adsorbent comprising at least one zeolite adsorbent as defined according to claim 1,
   b) bringing the bed of adsorbent into contact with a desorbent.

17. Process for recovering para-xylene according to claim 16, wherein the process is of simulated moving bed.

18. Process for recovering para-xylene from a feedstock comprising fractions of aromatic hydrocarbon isomers containing 8 carbon atoms, in the gas phase, by adsorption of the para-xylene by means of an adsorbent according to claim 1, comprising the following successive steps:
   a) bringing a feedstock into contact with a bed of adsorbent comprising at least one zeolite adsorbent as defined according to claim 1,
   b) bringing the bed of adsorbent into contact with a desorbent.

19. Process for separating a feedstock comprising polyhydric alcohols, comprising a step of bringing the feedstock into contact with an adsorbent as defined according to claim 1.

20. Process for separating a feedstock comprising isomers of substituted toluene, comprising a step of bringing the feedstock into contact with an adsorbent as defined according to claim 1.

21. Process for separating a feedstock comprising cresols, comprising a step of bringing the feedstock into contact with an adsorbent as defined according to claim 1.

* * * * *